US009868697B2

(12) United States Patent
Kim et al.

(10) Patent No.: US 9,868,697 B2
(45) Date of Patent: Jan. 16, 2018

(54) PHYTOSPHINGOSINE DERIVATIVES, AND COMPOSITION COMPRISING SAME FOR PREVENTING AND TREATING INFLAMMATORY SKIN DISEASES, AUTOIMMUNE DISEASES, AND HYPERKERATOSIS DISEASES

(71) Applicant: THE CATHOLIC UNIVERSITY OF KOREA INDUSTRY—ACADEMIC COOPERATION FOUNDATION, Seoul (KR)

(72) Inventors: Byung-Hak Kim, Seoul (KR); Tae-Yoon Kim, Seoul (KR); Sanghee Kim, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 134 days.

(21) Appl. No.: 14/299,746

(22) Filed: Jun. 9, 2014

(65) Prior Publication Data
US 2014/0343150 A1    Nov. 20, 2014

Related U.S. Application Data

(63) Continuation-in-part of application No. PCT/KR2012/010642, filed on Dec. 7, 2012.

(30) Foreign Application Priority Data

Dec. 7, 2011 (KR) ........................ 10-2011-0130560

(51) Int. Cl.
| C07C 235/74 | (2006.01) |
| C07C 231/02 | (2006.01) |
| A61Q 19/00  | (2006.01) |
| C07C 235/76 | (2006.01) |
| A61K 8/68   | (2006.01) |
| A61K 31/197 | (2006.01) |

(52) U.S. Cl.
CPC .............. *C07C 235/74* (2013.01); *A61K 8/68* (2013.01); *A61K 31/197* (2013.01); *A61Q 19/00* (2013.01); *C07C 231/02* (2013.01); *C07C 235/76* (2013.01)

(58) Field of Classification Search
None
See application file for complete search history.

(56) References Cited

U.S. PATENT DOCUMENTS

| 5,919,960 A    | 7/1999 | Weber et al. |
| 8,246,972 B2   | 8/2012 | Allart et al. |
| 2003/0064936 A1| 4/2003 | Nieuwenhuizen et al. |
| 2006/0166934 A1| 7/2006 | Kim et al. |
| 2009/0176888 A1| 7/2009 | Lee et al. |

FOREIGN PATENT DOCUMENTS

| JP | 2000-191496    | 7/2000  |
| KR | 10-2002-0042606| 6/2002  |
| KR | 10-2004-0016353| 2/2004  |
| KR | 10-2007-0098078| 10/2007 |
| KR | 10-2010-0070109| 6/2010  |
| KR | 10-2010-0104634| 9/2010  |

OTHER PUBLICATIONS

International Search Report dated Apr. 5, 2013 in International Application No. PCT/KR2012/010642.
Written Opinion dated Apr. 5, 2013 in International Application No. PCT/KR2012/010642.
B.S. Moon et al., "Synthesis of novel phytosphingosine derivatives and their preliminary biological evaluation for enhancing radiation therapy", Bioorganic & Medicinal Chemistry Letters, vol. 17, pp. 6643-6646, 2007.
T. Pavicic, et al., "Anti-microbial and -inflammatory activity and efficacy of phytosphingosine: an in vitro and in vivo study addressing acne vulgaris", Int'l Journal of Cosmetic Science, vol. 29, pp. 181-190, 2007.
Fischer, et al., "Antibacterial activity of sphingoid bases and fatty acids against Gram-positive and Gram-negative bacteria", Antimicrobial Agents and Chemotherapy, vol. 56, No. 3, pp. 1157-1161, Mar. 2012.
Kim, et al., "Differential regulation of cyclooxygenase-2 expression by phytosphingosine derivatives, NAPS and TAPS, and its role in the NAPS or TAPS-mediated apoptosis", The Journal of Investigative Dermatology, vol. 121, No. 5, pp. 1126-1134, Nov. 2003.
Kim et al., "Potentiation of UVB-induced apoptosis by novel phytosphingosine derivative tetraacetyl phytosphingosine in HaCaT cell and mouse skin", Apoptosis, vol. 9, No. 4, pp. 449-456, 2004.
Kim, et al., "N,N-dimethyl phytosphingosine induces caspase-8-dependent cytochrome c release and apoptosis through ROS generation in human leukemia cells", Toxicology and Applied Pharmacology, vol. 239, No. 1, pp. 87-97, 2009.
De Vry, et al., "Topical application of a novel immunomodulatory peptide, RDP58, reduces skin inflammation in the phorbol ester-induced dermatitis model", The Journal of Investigative Dermatology, vol. 125, No. 3, pp. 473-481, Sep. 2005.
Zheng, et al., "Interleukin-22, a T(H)17 cytokine, mediates IL-23-induced dermal inflammation and acanthosis", Nature, vol. 445, pp. 648-651, Feb. 8, 2007.
Kumar, et al., "Embelin reduces cutaneous TNF-α level and ameliorates skin edema in acute and chronic model of skin inflammation in mice", European Journal of Pharmacology, vol. 662, pp. 63-69, 2011.

(Continued)

*Primary Examiner* — Kortney L. Klinkel
*Assistant Examiner* — William Lee
(74) *Attorney, Agent, or Firm* — H.C. Park & Associates, PLC

(57) ABSTRACT

A phytosphingosine derivative of chemical formula IA or IB, and a composition comprising the phytosphingosine derivative for preventing and treating inflammatory skin diseases, autoimmune diseases, and hyperkeratotic diseases. The phytosphingosine derivatives of the present disclosure are involved with transcription factors related to inflammation, autoimmune diseases and hyperkeratotic diseases, the expression and the generation of inflammatory mediators, signal transduction mechanisms, and the expression and the activity of relevant enzymes and the like.

6 Claims, 21 Drawing Sheets

(56) References Cited

OTHER PUBLICATIONS

Maddur, et al., "Th17 cells: biology, pathogenesis of autoimmune and inflammatory diseases, and therapeutic strategies", The American Journal of Pathology, vol. 181, No. 1, pp. 8-18, Jul. 2012.

International Search Report dated Mar. 26, 2013 in International Application No. PCT/KR2012/010643.
Written Opinion dated Mar. 26, 2013 in International Application No. PCT/KR2012/010643.
Non Final Office Action dated Sep. 18, 2015, in U.S. Appl. No. 14/299,816.
Final Office Action dated Apr. 6, 2016, in U.S. Appl. No. 14/299,816.

[FIG. 1A]
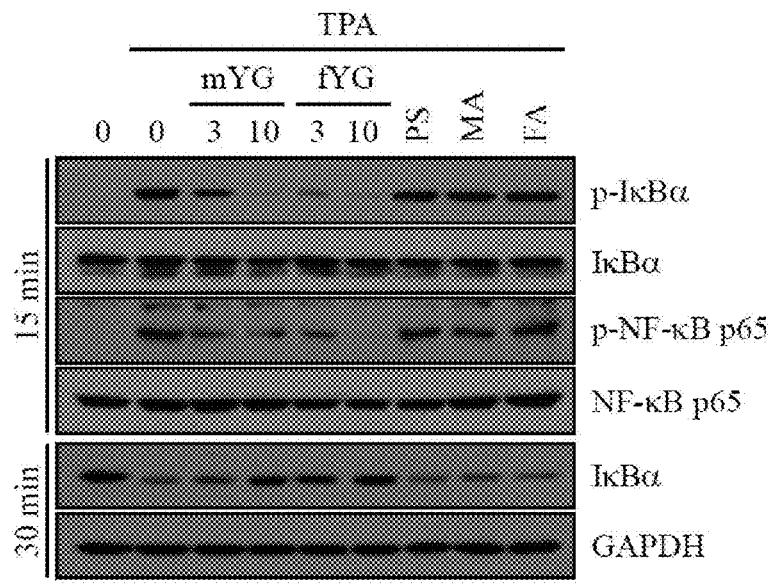
[FIG. 1B]
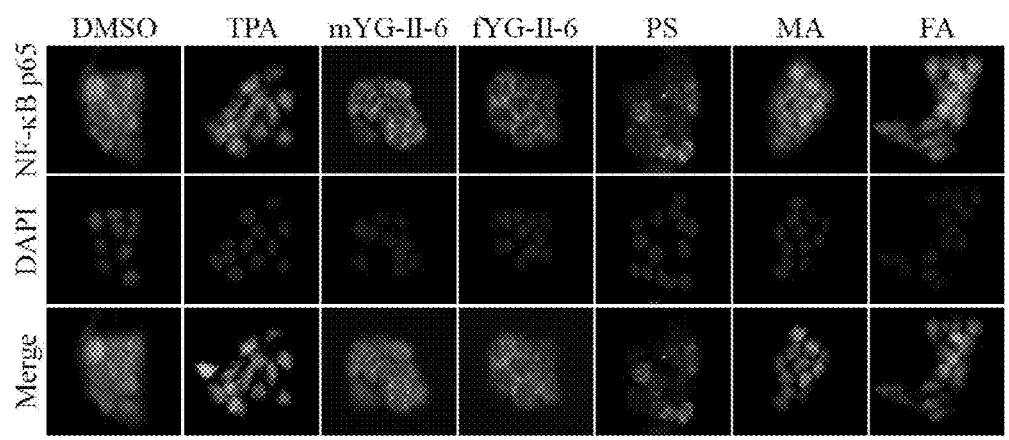

[FIG. 1C]
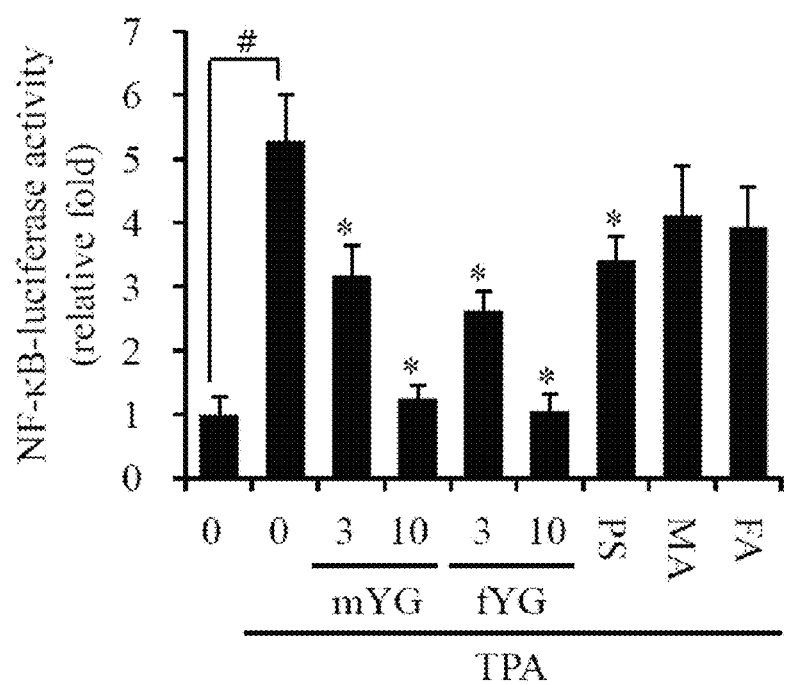

[FIG. 1D]
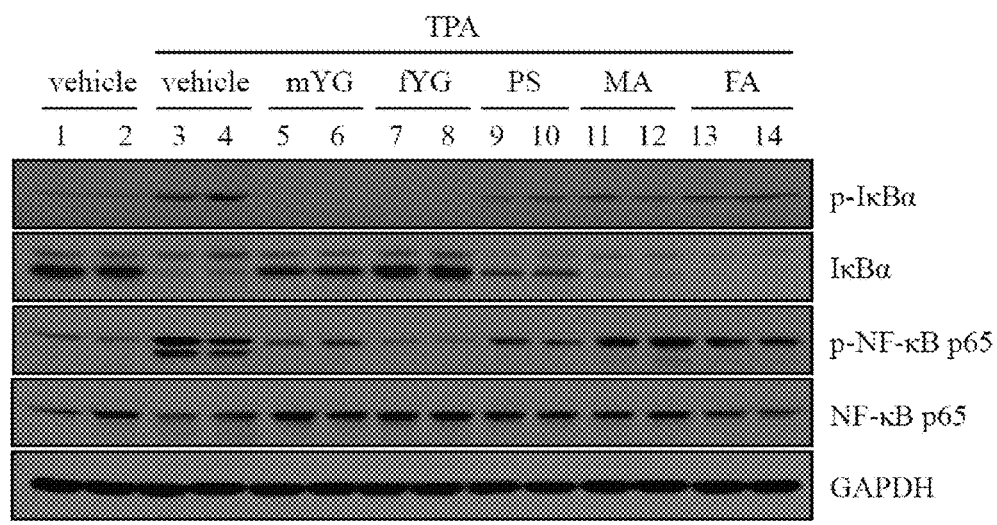

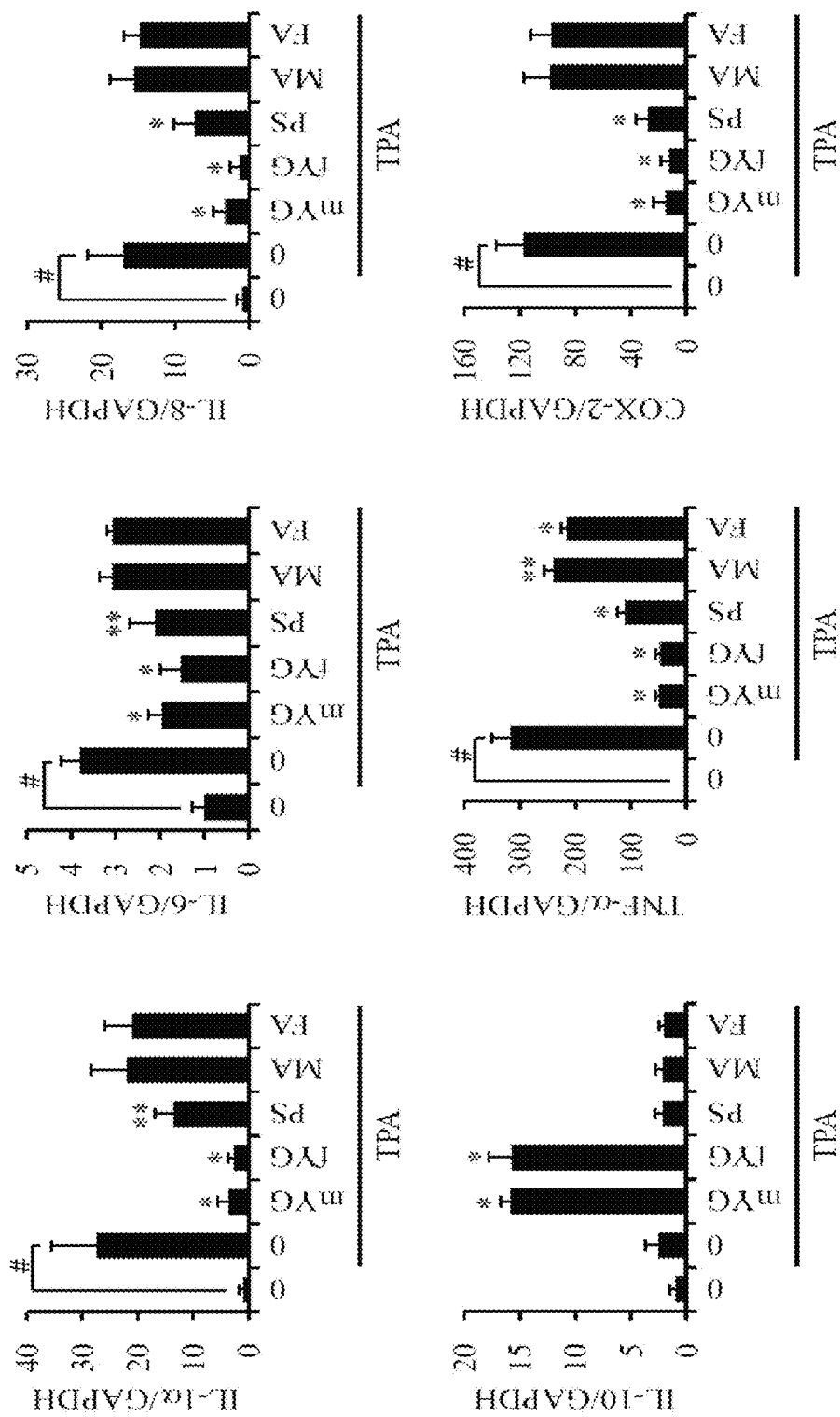
[FIG. 2]

[FIG. 3A]
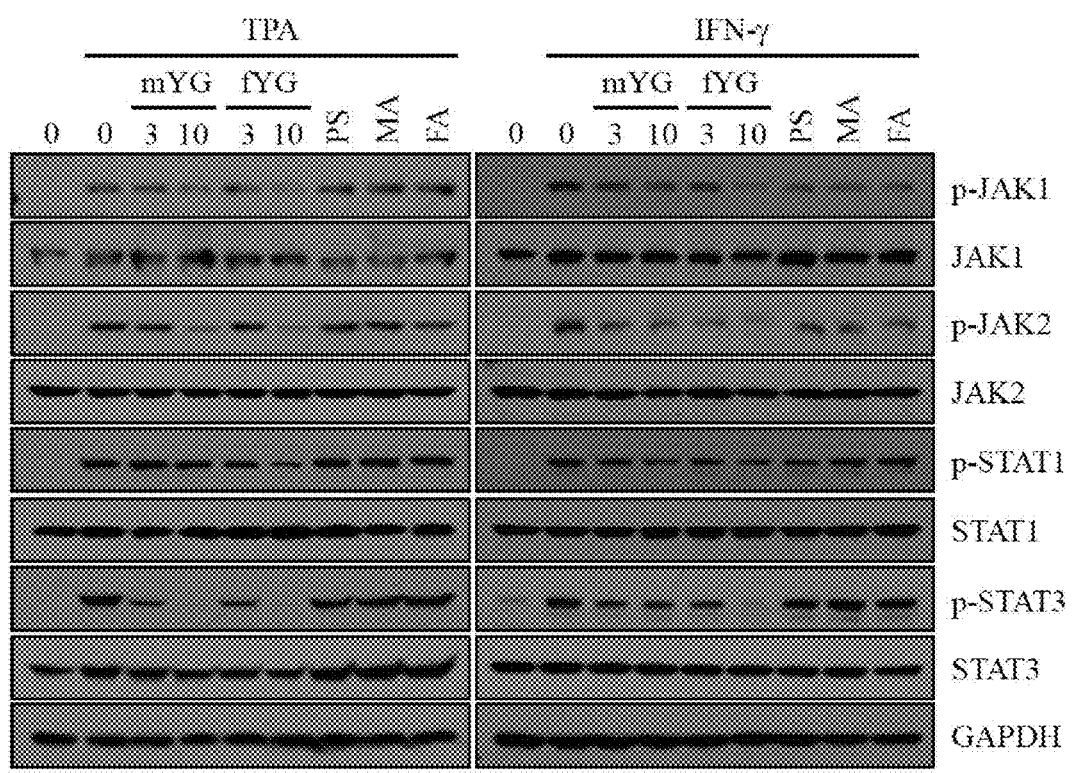

[FIG. 3B]
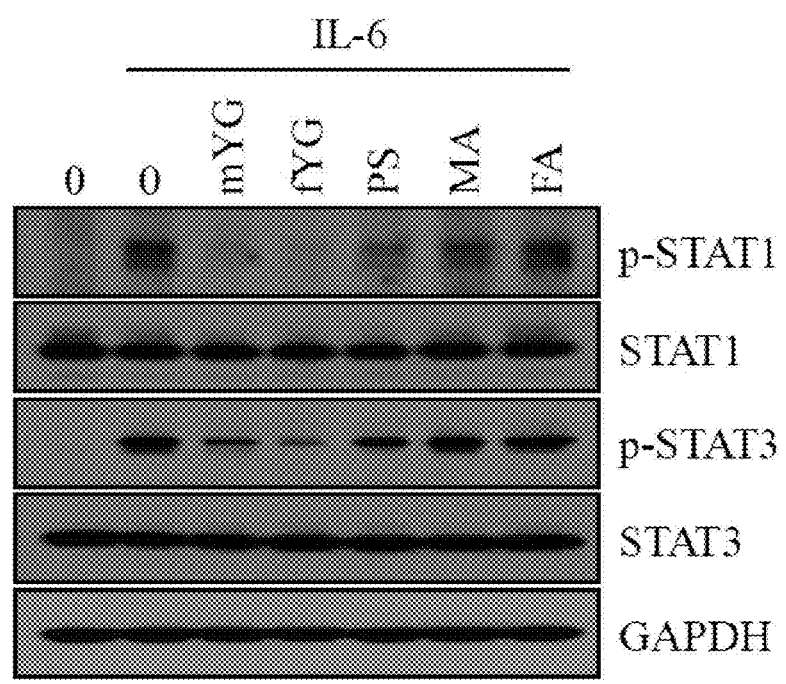

[FIG. 3C]
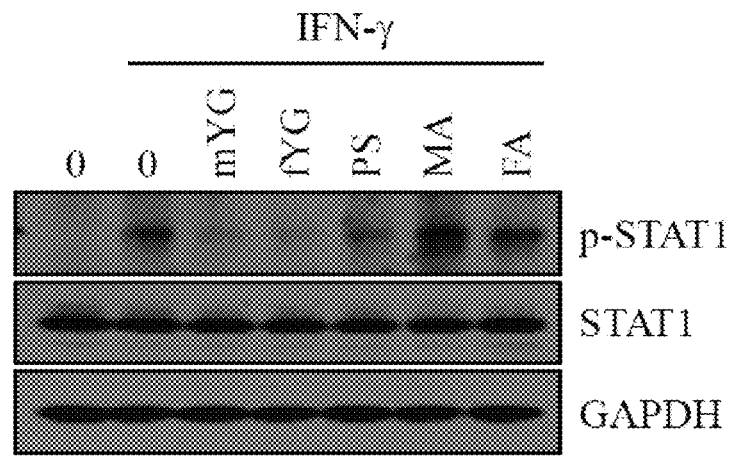
[FIG. 3D]
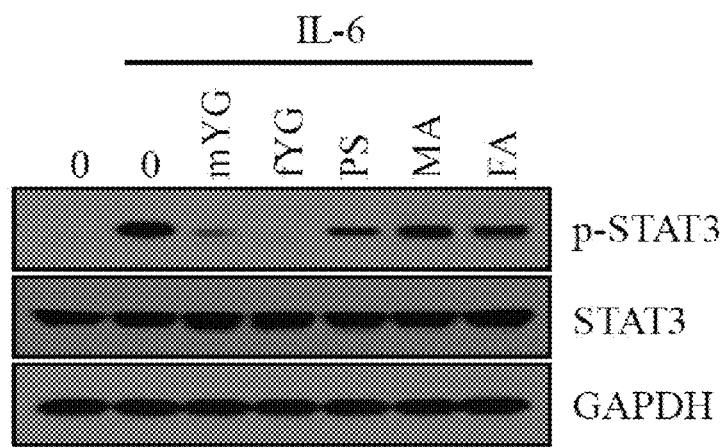

[FIG. 3E]
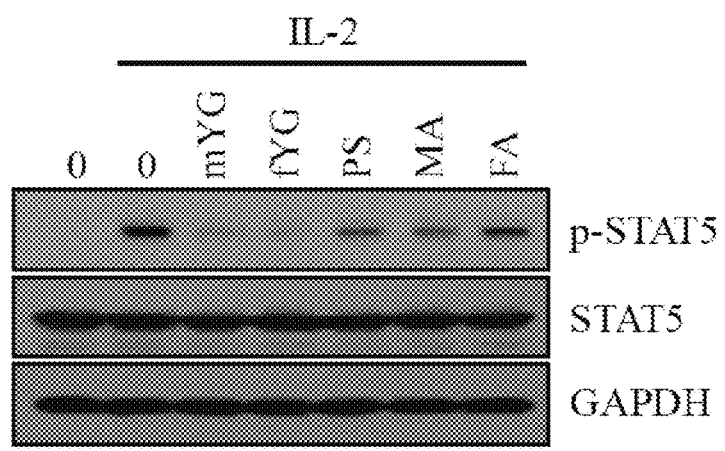

[FIG. 3F]
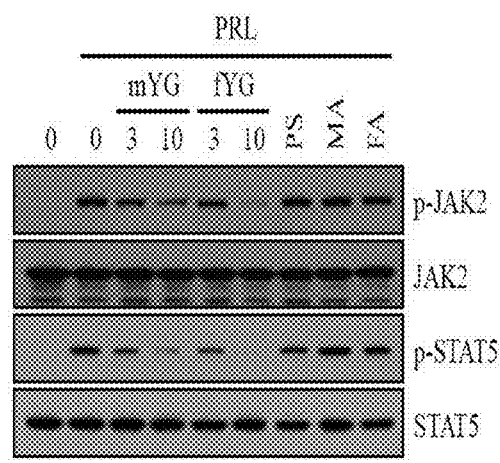
[FIG. 3G]
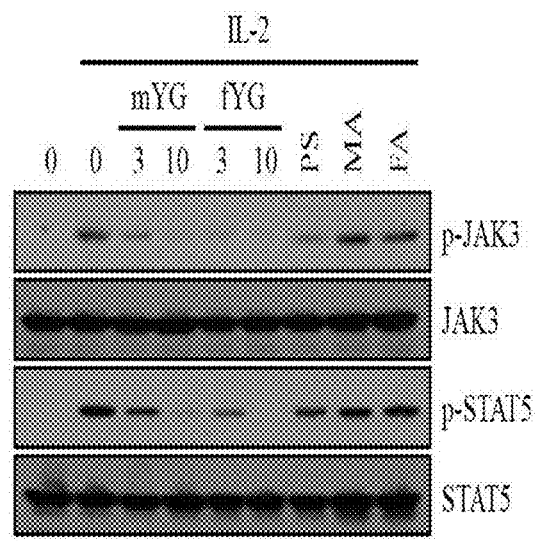

[FIG. 4]
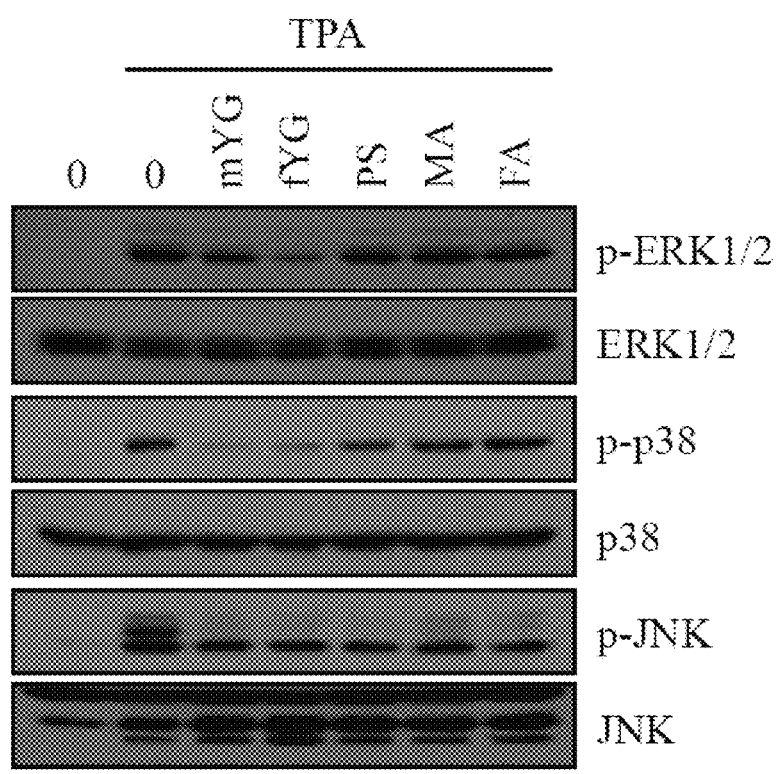

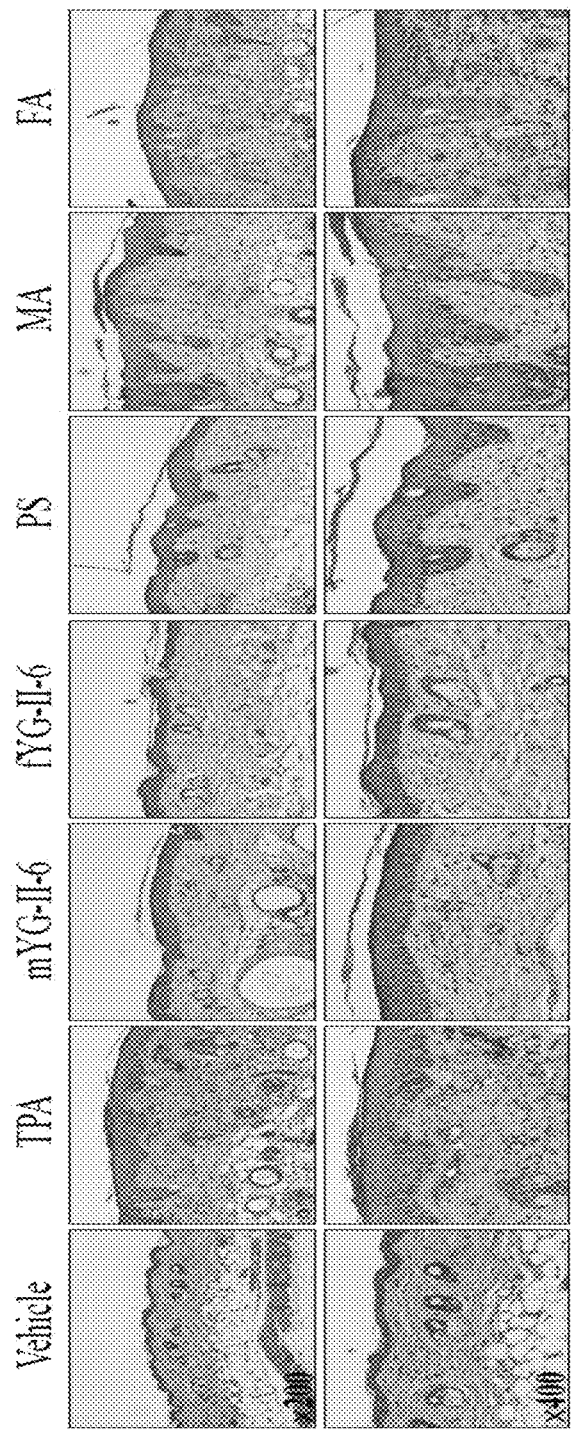
[FIG. 5A]

[FIG. 5B]
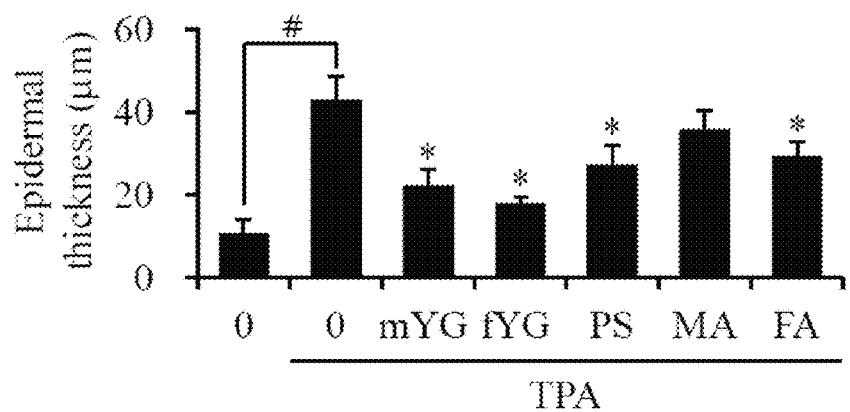
[FIG. 5C]
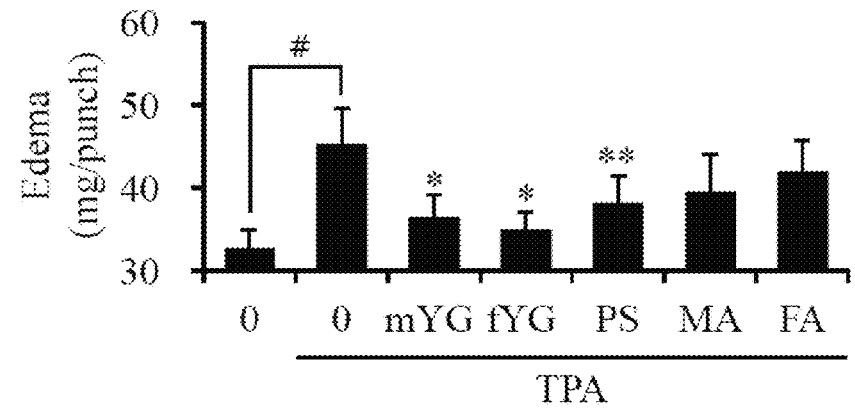

[FIG. 5D]
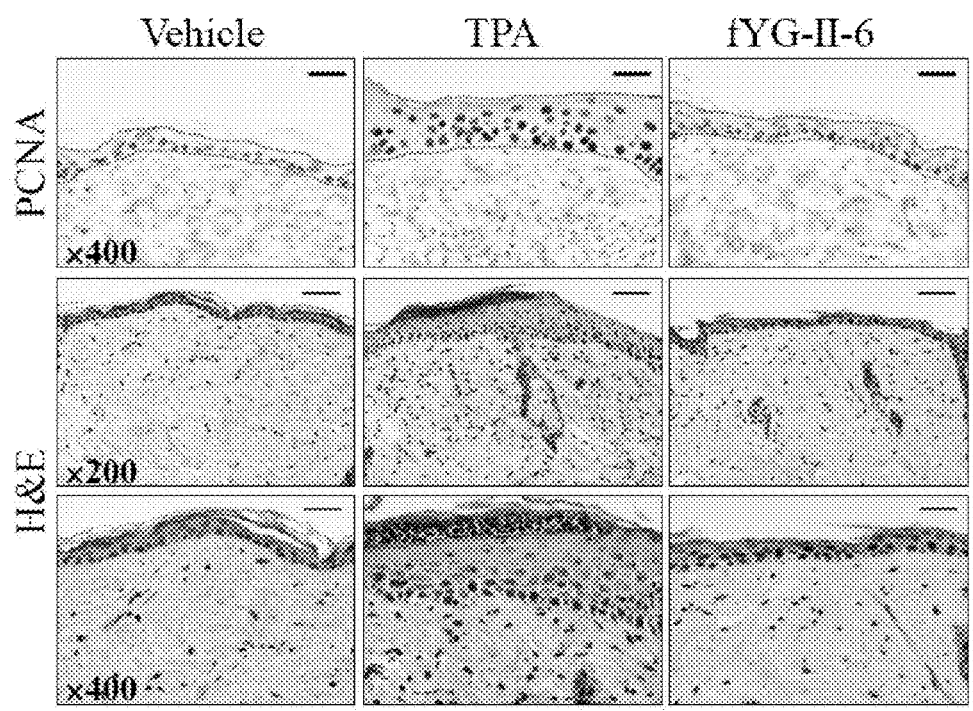

[FIG. 6A]
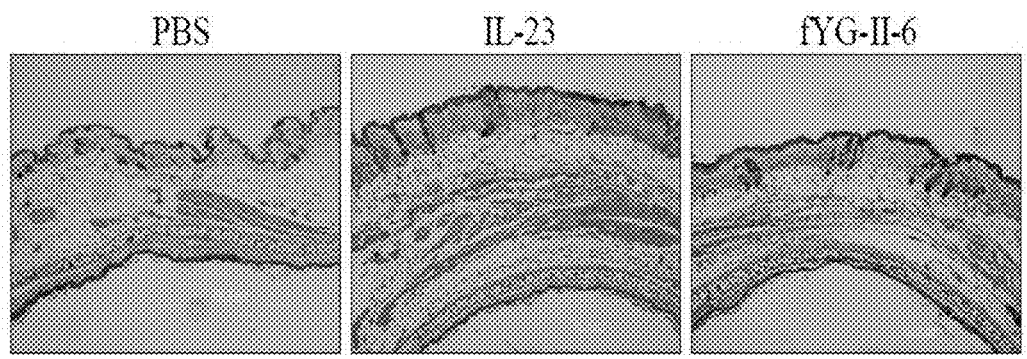
[FIG. 6B]
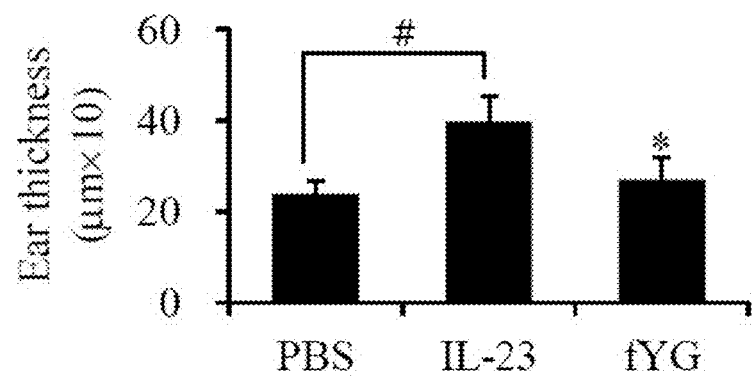

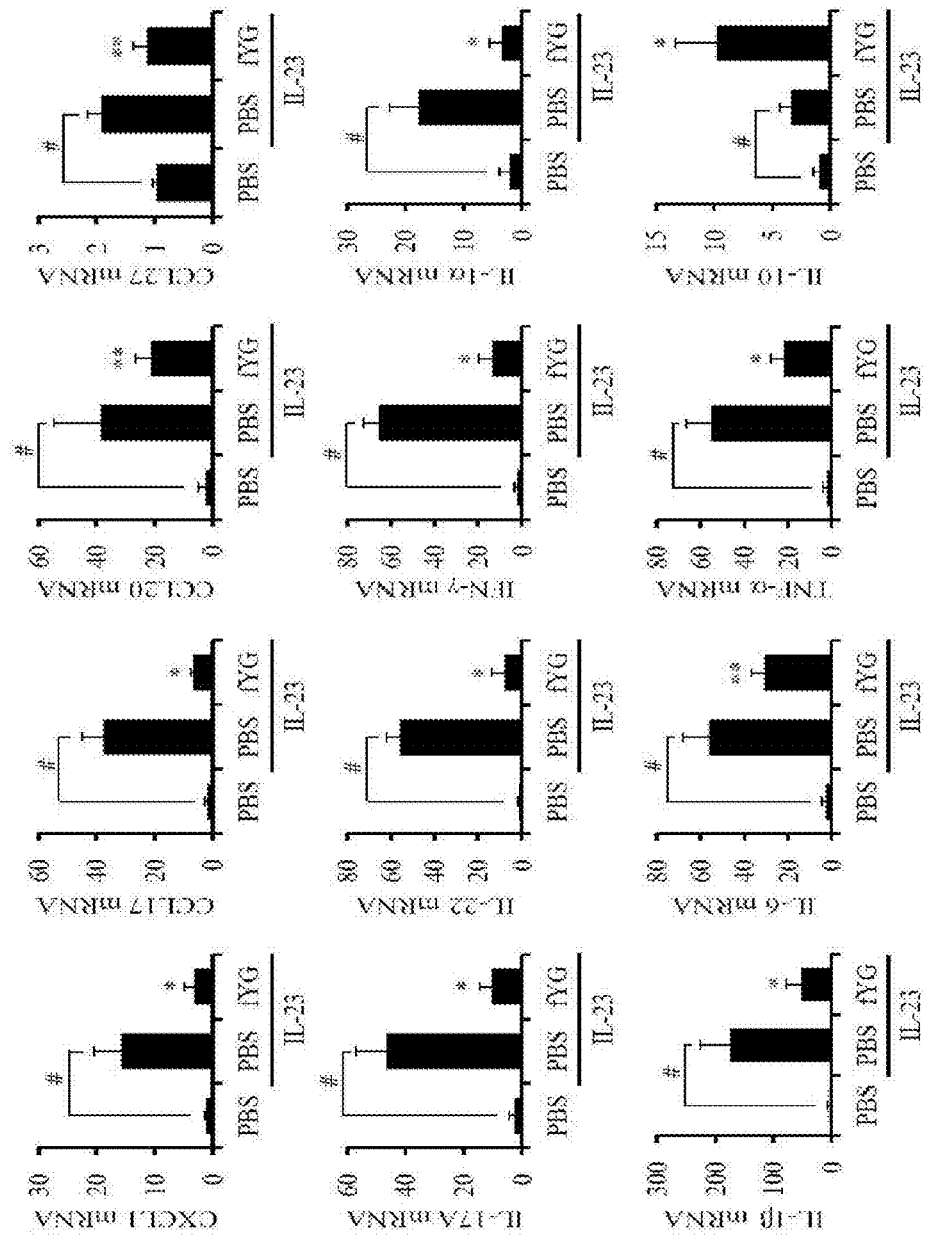
[FIG. 6C]

[FIG. 6D]
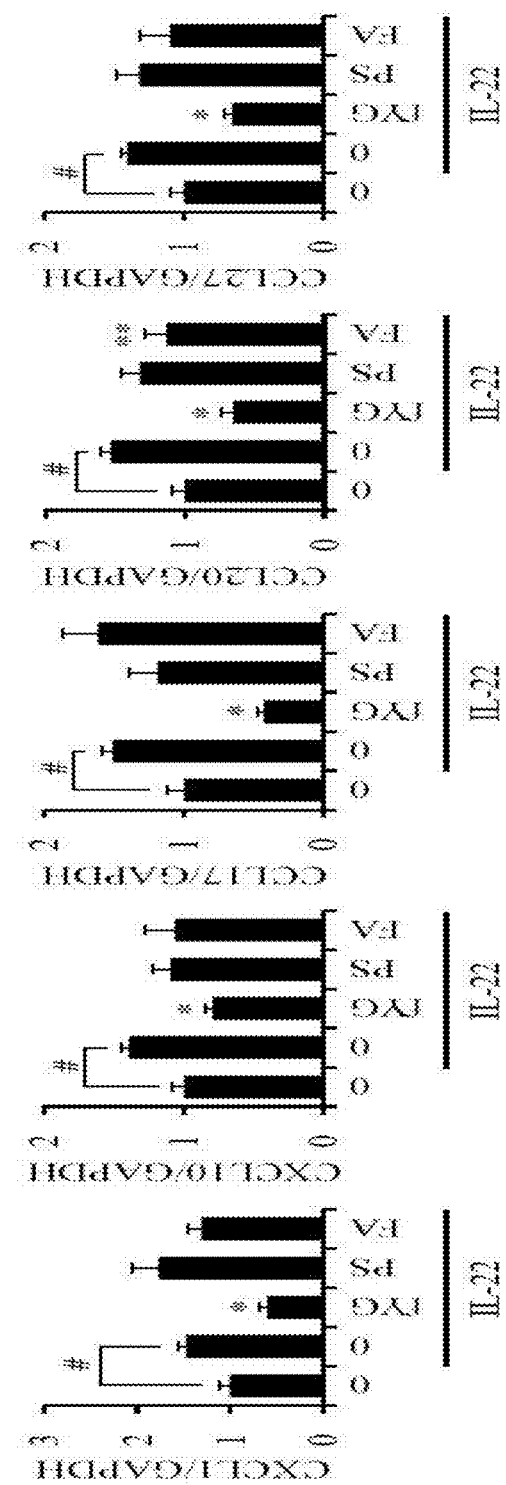

[FIG. 7A]
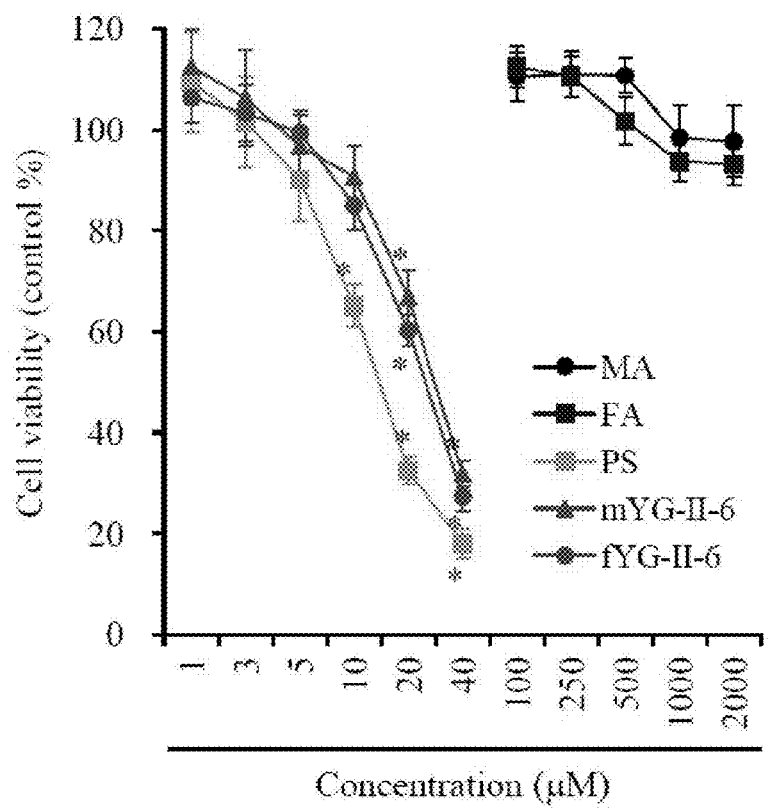

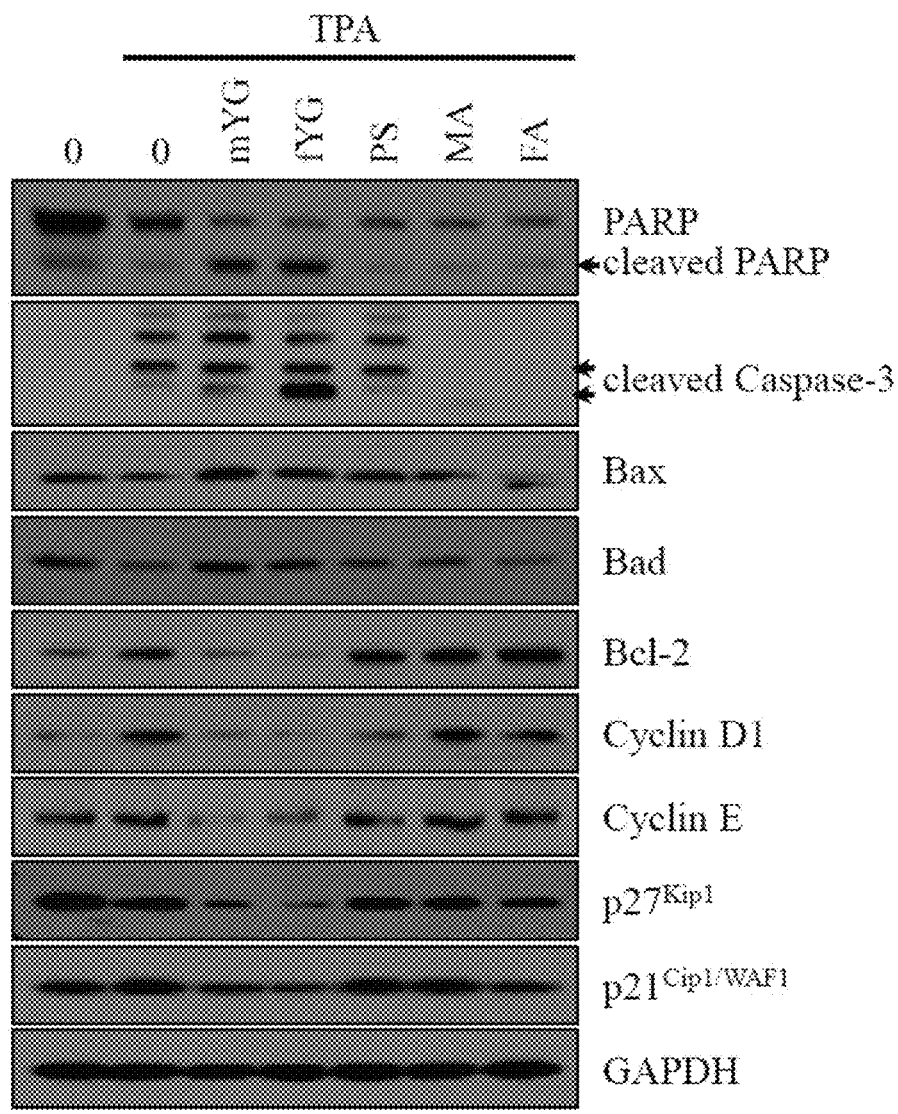
[FIG. 7B]

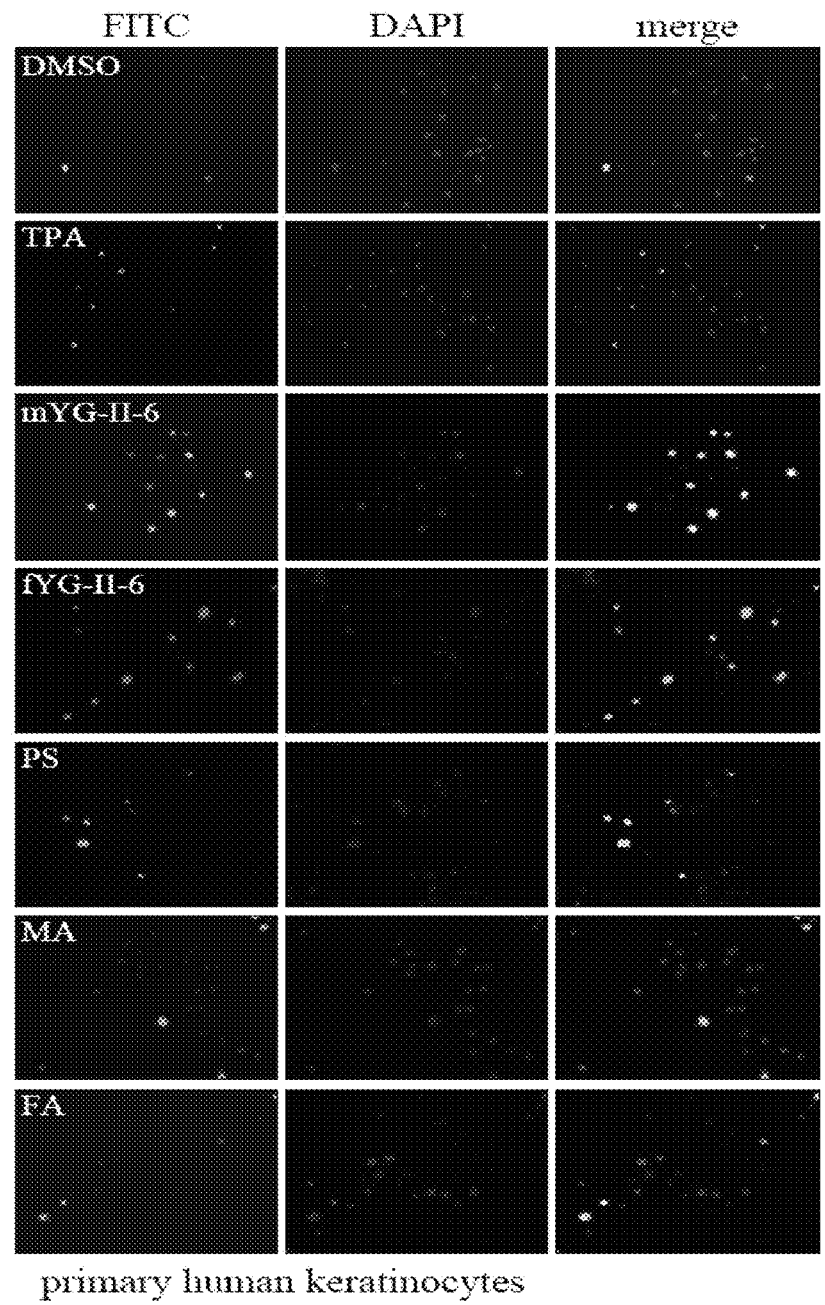
[FIG. 7C]
primary human keratinocytes

[FIG. 7D]
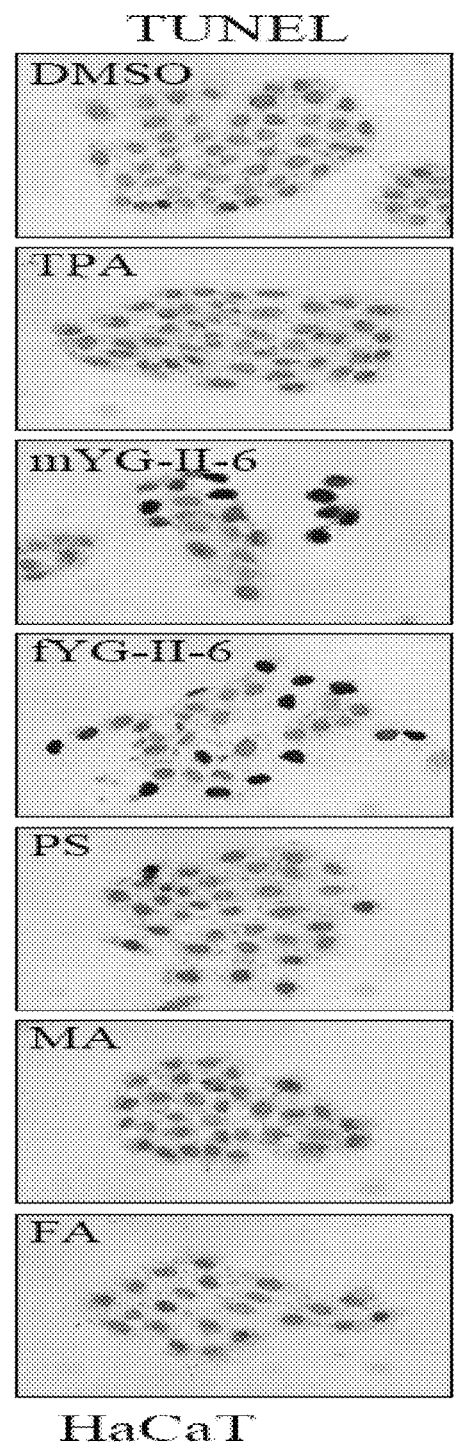

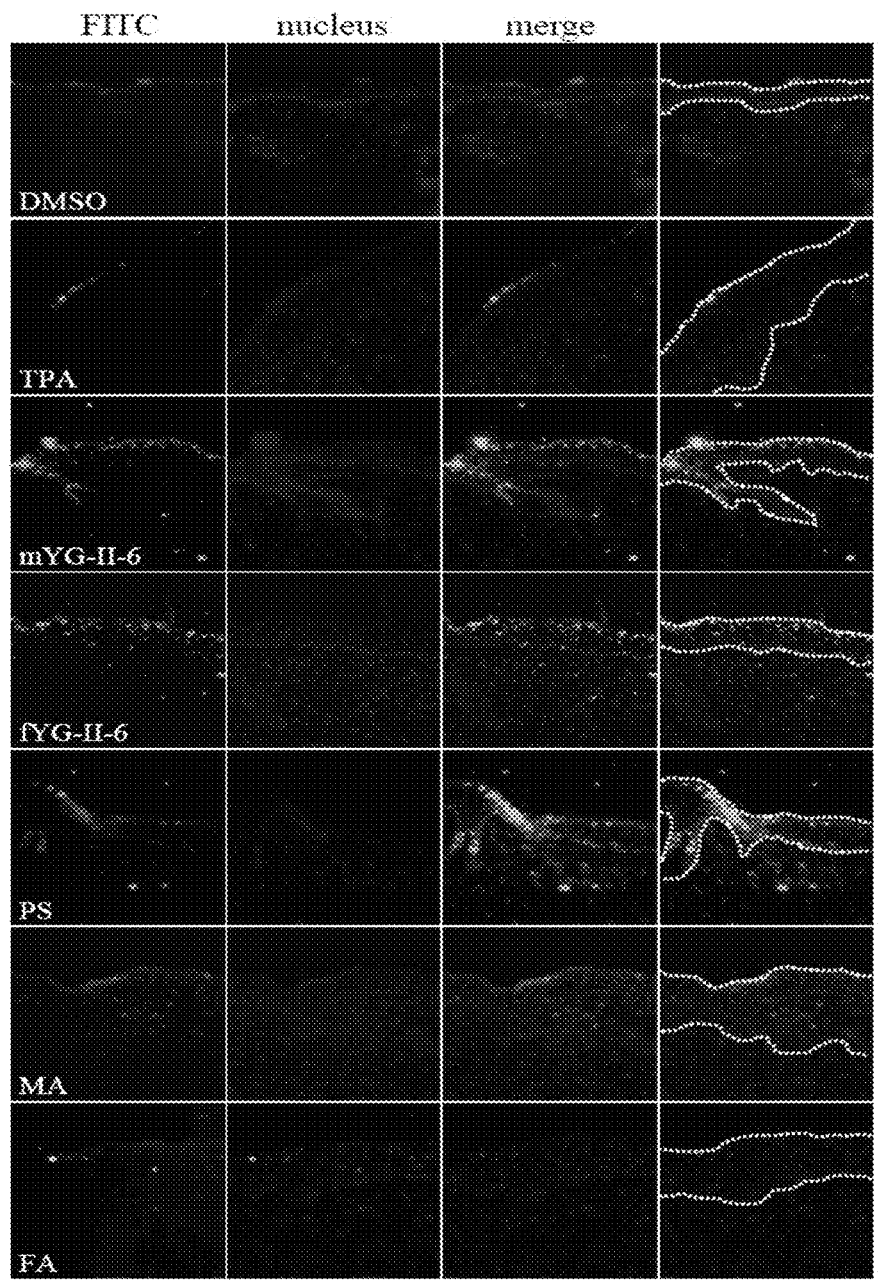
[FIG. 7E]

PHYTOSPHINGOSINE DERIVATIVES, AND COMPOSITION COMPRISING SAME FOR PREVENTING AND TREATING INFLAMMATORY SKIN DISEASES, AUTOIMMUNE DISEASES, AND HYPERKERATOSIS DISEASES

CROSS REFERENCE TO RELATED APPLICATIONS

This application is a continuation in part of the International Application No. PCT/KR2012/010642, filed on Dec. 7, 2012, and claims priority from and the benefit of Korean Patent Application No. 10-2011-0130560, filed on Dec. 7, 2011, all of which are hereby incorporated by reference for all purposes as if fully set forth herein.

BACKGROUND

Field

The present disclosure relates to novel phytosphingosine derivatives and compositions comprising the same, for preventing and treating inflammatory skin diseases and autoimmune diseases, and more particularly, to phytosphingosine derivatives of Chemical Formulas IA and IB, and compositions comprising the same for preventing and treating inflammatory skin diseases, autoimmune diseases, and hyperkeratotic disorders.

Discussion of the Background

Phytosphingosine is a lipid having a skeletal structure of spingosine, which is abundant in fungi, plants, and the skin of animals including humans. In particular, phytosphingosine serves as a precursor of ceramide, which is an integral part of the lipid bilayer of the stratum corneum of the skin, to prevent the moisture loss from the skin, thereby moisturizing the skin and preventing easy absorption of foreign harmful materials into the dermal layer of the skin. In addition, phytosphingosine is absorbed in the body to promote the synthesis of ceramides, and has antimicrobial activity against several microorganism including Propionibacterium acnes and Staphylococcus aureus, and thus, is included in products for the treatment of acne and the like.

Phytosphingosine and phytosphingosine derivatives such as N-acetyl phytosphingosine (NAPS) and tetra-acetyl phytosphingosine (TAPS) regulate the expression of cyclooxygenase-2 (COX-2) in skin keratinocytes, induce apoptosis through activation of caspase-8 and mitochondria, suppress skin keratinocyte hyperproliferation against external stimuli, and regulate skin inflammation responses. However, since they cause damage to the liver and the kidneys, cause gastrointestinal disorders and accompanying dizziness and vomiting, and have severe cytotoxicity, their disadvantages due to cytotoxicity outweigh their advantages as a therapeutic agent, and as a result, they are difficult to use as an agent for treating skin diseases or other diseases.

Maleic acid is the geometric isomer (having the same molecular formula) of fumaric acid, and is used as an acidulant for giving a tart taste in juice, cider, canned fruits, and the like. Maleic anhydride generated through heating is widely used in the preparation of unsaturated polyester resins, copolymers with styrene, and various synthetic chemicals by reacting with various materials using catalysts.

The present inventors have synthesized phytosphingosine derivatives (mYG-II-6 and fYG-II-6) having an anti-inflammatory effect while overcoming disadvantages of phytosphingosine by using phytosphingosine (PS) and maleic anhydride (MA) or fumaric acid (FA), and as a result, provided materials and a pharmaceutical composition exhibiting excellent effects in the treatment and prevention of inflammatory skin diseases, autoimmune diseases, and hyperkeratotic disorders.

SUMMARY

Aspects of the present disclosure provide novel compounds synthesized using phytosphingosine and maleic anhydride, which are more effective than phytosphingosine in terms of the treatment and prevention of inflammatory skin diseases, autoimmune diseases, and hyperkeratotic disorders, and also overcome disadvantages of phytosphingosine.

Accordingly, an aspect of the present disclosure is to provide a phytosphingosine derivative of Chemical Formulas IA and IB below:

[Chemical Formula IA]

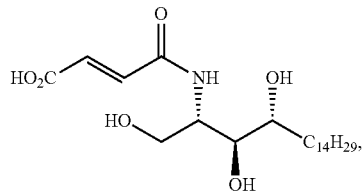

[Chemical Formula IB]

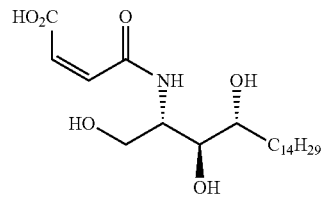

Another aspect of the present disclosure provides a pharmaceutical composition for preventing and treating inflammatory skin diseases and autoimmune diseases, comprising the phytosphingosine derivative and/or its pharmaceutically acceptable salt as an active ingredient.

Another aspect of the present disclosure is to provide a pharmaceutical composition for preventing and treating hyperkeratotic disorders, comprising the phytosphingosine derivative and/or its pharmaceutically acceptable salt, as an active ingredient.

Still another aspect of the present disclosure provides a method for preparing the phytosphingosine derivative, the method comprising: (a) reacting phytosphingosine (PS) with maleic anhydride (MA) or fumaric acid (FA) in an organic solvent; and (b) separating the phytosphingosine derivative from the resulting reaction product.

Still another aspect of the present disclosure provides a method for preventing and treating an inflammatory skin disease, an autoimmune disease and/or a hyperkeratotic disorder, the method comprising administering to a subject in need thereof an effective amount of the phytosphingosine derivative or its pharmaceutically acceptable salt.

In accordance with still further aspect of the present disclosure, there is provided a method for preventing and treating an inflammatory skin disease, an autoimmune disease and/or a hyperkeratotic disorder, the method comprising administering to a subject in need thereof an effective amount of the phytosphingosine derivative or its pharmaceutically acceptable salt.

BRIEF DESCRIPTION OF THE DRAWINGS

The accompanying drawings, which are included to provide a further understanding of the invention and are incorporated in and constitute a part of this specification, illustrate embodiments of the disclosure, and together with the description serve to explain the principles of the disclosure.

FIGS. 1A-1D illustrate results showing the effects of the phytosphingosine derivatives of the present disclosure on NF-κB signaling.

FIG. 2 illustrates results showing the effects of the phytosphingosine derivatives on the expression and the generation of inflammatory mediators.

FIGS. 3A-3G illustrate results showing the activity of the phytosphingosine derivatives on JAK/STAT signaling.

FIG. 4 illustrates results showing the effects of the phytosphingosine derivatives on the MAP kinase.

FIGS. 5A-5D illustrate results showing the activity of the phytosphingosine derivatives on the inhibition of TPA-induced skin inflammation and apoptosis.

FIGS. 6A-6D illustrate results showing the effects of the phytosphingosine derivatives on IL-23-induced psoriasiform skin diseases.

FIGS. 7A-7E illustrate results showing cytotoxicity and apoptosis of phytosphingosine in human derived keratinocytes and mouse skins.

DETAILED DESCRIPTION OF THE ILLUSTRATED EMBODIMENTS

The present disclosure provides phytosphingosine derivatives of Chemical Formula I (called ((E)-4-oxo-4-(((2S,3S,4R)-1,3,4-trihydroxyoctadecan-2-yl)amino)but-2-enoic acid; fYG-II-6; and Chemical Formula IB (Z)-4-oxo-4-(((2S,3S,4R)-1,3,4-trihydroxyoctadecan-2-yl)amino)but-2-enoic acid; mYG-II-6):

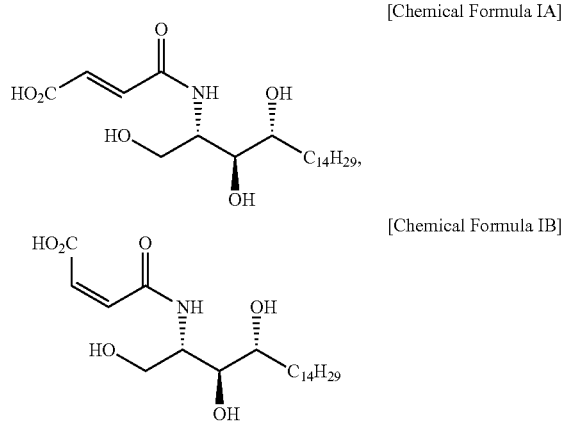

[Chemical Formula IA]

[Chemical Formula IB]

Phytosphingosine represented by the following Chemical Formula II serves as a precursor of ceramide, which is an integral part of the lipid bilayer of the skin, to have various defense actions, such as preventing moisture loss from the skin, regulating an antimicrobial activity and controlling skin inflammation, and thus, is considered an essential component of the human body. However, phytosphingosine is difficult to use as a therapeutic agent, due to its toxicity outweighing its advantages as a therapeutic agent.

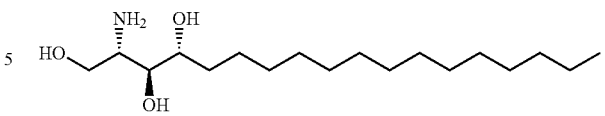

[Chemical Formula II]

However, the addition of maleic anhydride or fumaric acid, which are represented by Chemical Formulas III and IV below, to phytosphingosine, leads to a phytosphingosine derivative that has excellent effect in the prevention, treatment, and amelioration of inflammatory skin diseases, autoimmune diseases, and hyperkeratotic disorders, while overcoming disadvantages of phytosphingosine caused by its toxicity.

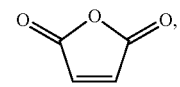

[Chemical Formula III]

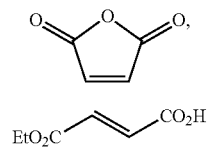

[Chemical Formula IV]

Further, the phytosphingosine derivatives according to the present disclosure are much more effective than phytosphingosine in preventing, ameliorating, and treating inflammatory skin diseases, autoimmune diseases, and hyperkeratotic disorders.

In an exemplary embodiment of the present disclosure, it was verified that the phytosphingosine derivatives according to the present disclosure inhibit the phosphorylation and degradation of IκB associated with the activation of NF-κB in TPA-stimulated skin keratinocytes and primary culture skin keratinocytes, thereby inhibiting transcriptional activity and phosphorylation of NF-κB and the nuclear translocation of NF-κB. These two types of YG-II-6 compounds were found to be more effective than phytosphingosine used as a synthetic precursor, in terms of inhibiting NF-κB activity (See FIGS. 1A-1D).

In addition, as for their effects on the inflammatory mediator, both of the two phytosphingosine derivatives effectively inhibited the gene expression of COX-2 due to TPA stimulation, and the gene expression of IL-1α, IL-6, IL-8, and TNF-α, which are representative inflammatory mediators (See FIG. 2).

When different JAK/STAT signaling pathways were activated with respect to stimulations by various cytokines including TPA in human-derived skin keratinocytes, mononuclear cells, mouse T cells, and mouse-derived lymphoma cells, both of the two phytosphingosine derivatives inhibited these pathways, and their inhibitory effects were more effective than those of phytosphingosine (See FIGS. 3A-3g).

It was found that phytosphingosine showed no or little inhibitory effect on the MAP kinase, whereas both of the two YG-II-6 compounds strongly inhibited the phosphorylation of ERK1/2, p38, and JNK (See FIG. 4).

As for the effect on inflammatory skin diseases in a skin disease animal model, the two phytosphingosine derivatives remarkably suppressed epidermal hyperplasia, hyperkeratosis, and translocation of inflammatory cells into the dermis, which are skin inflammatory responses increased by TPA stimulation. Further, in the patch test on the dorsal skin of hairless mice, the phytosphingosine derivatives remarkably suppressed skin inflammatory responses, epidermal hyperplasia, hyperkeratosis, and translocation of inflammatory cells into the dermis (See FIGS. 5A-5D). In addition, as for the IL-23-induced psoriasiform skin diseases, the phytosphingosine derivatives remarkably suppressed epidermal hyperplasia, hyperkeratosis, and translocation of inflammatory cells into the dermis, which are lesions of psoriasis diseases, and significantly inhibited the expression of cytokines and chemokines associated with these diseases. In addition, the phytosphingosine derivatives remarkably inhibited the expression of representative genes which have been known to be associated with psoriasis diseases in the psoriasiform disease environment by the IL-22-stimulated human derived keratinocytes (See FIGS. 6A-6D).

The two newly synthesized phytosphingosine derivatives reduced cytotoxicity and relatively increased apoptotic pathways during cellular apoptosis, in comparison with their precursor phytosphingosine (See FIGS. 7A-7E).

It has been generally known that external stimulation-induced skin swelling, epidermal hyperplasia, hyperkeratosis, and translocation of inflammatory cells into the dermis due to increased blood vessel permeability are representative symptoms caused by inflammatory responses, while activating NF-κB and JAK/STAT signaling pathways to increase expression and generation of various cytokines, chemokines, and enzymes known to induce various types of inflammation. Various inflammatory mediators generated by inflammatory responses may lead to render inflammatory diseases chronic, causing autoimmune diseases. These diseases continuously cause skin swelling and skin keratinocyte hyperproliferation (epidermal hyperplasia), and thus lead to hyperkeratosis in which the epidermis of the skin is thickened and cornified (References 6 to 9).

Therefore, the two phytosphingosine derivatives effectively inhibited the activation of NF-κB and JAK/STAT signaling pathways, which are representative signaling pathways known to be activated by external stimulation to cause diseases associated with inflammation, thereby exhibiting excellent inhibitory activity on skin inflammation and autoimmune diseases including psoriasis, and were less cytotoxic than phytosphingosine used as a control group.

Accordingly, the phytosphingosine derivatives of Chemical Formulas IA and IB, which are compounds newly synthesized by using phytosphingosine (PS) and maleic anhydride (MA) or fumaric acid (FA), possess a weak cytotoxicity and an excellent pharmacological activity as compared with phytosphingosine used as a precursor. Thus, the phytosphingosine derivatives can be used in the preparation of a pharmaceutical composition or cosmetic composition for preventing, treating, and ameliorating inflammatory skin diseases and autoimmune diseases, or cosmetic compositions.

The present disclosure provides a pharmaceutical composition for preventing and treating inflammatory skin diseases, autoimmune diseases, and hyperkeratotic disorders, comprising the phytosphingosine derivative or its pharmaceutically acceptable salt, as an active ingredient.

Examples of the inflammatory skin diseases may include, but are not limited to, atopic dermatitis, systemic lupus erythematosus, contact dermatitis, allergic skin diseases, acne, urticaria, and the like.

In addition, examples of the autoimmune diseases may include, but are not limited to, rheumatoid arthritis, systemic sclerosis, systemic lupus erythematosus, psoriasis, asthma, ulcerative colitis, Crohn's disease, Veche's disease, dermatomyositis, multiple sclerosis, collagenosis, vasculitis, arthritis, granulomatosis, organ-specific autoimmune diseases, ulcerative colitis, graft-versus-host disease (GvHD), and the like.

In addition, examples of the hyperkeratotic disorders may include, but are not limited to, Grover diseases (transient acantholytic dermatosis), corns, calluses, warts, chronic eczema, lichen planus, actinic keratosis, seborrheic keratosis, ichthyosis, and the like.

The hyperkeratotic disorder causes the thickening of the outer layer of the skin, which contains a tough protective protein called keratin. This skin thickening is a part of the skin's normal protection against rubbing, pressure, and other forms of local irritation. It causes calluses and corns on hands and feet and whitish areas inside the mouth. Other forms of hyperkeratotic disorder may occur as part of the skin's defense against chronic inflammation, infection, sunlight damage, irritating chemicals, and the like. Less often, the hyperkeratotic disorder develops on the skin that has not been irritated. These types of hyperkeratotic disorders may be part of an inherited condition which may begin right after birth and may affect large areas of the skin.

The composition may comprise the phytosphingosine derivative according to the present disclosure or its pharmaceutically acceptable salt, alone or in combination with one or more pharmaceutically acceptable carrier, excipient, or diluent.

As used herein, the "pharmaceutically acceptable salt" refers to a salt that is physiologically acceptable and usually does not invoke allergic or similar reactions when administered to humans. Preferably, the salt may be an acid addition salt formed from a pharmaceutically acceptable free acid. The free acid may be an organic or inorganic acid. The organic acid includes, but is not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. Further, the inorganic acid includes, but is not limited to, hydrochloric acid, bromic acid, sulfuric acid and phosphoric acid.

A pharmaceutically acceptable carrier may include, for example, a parenteral or an oral preparation. The carriers for the oral preparation may include lactose, starch, cellulose derivatives, magnesium stearate, stearic acid. The carriers for the parenteral preparation may include water, suitable oil, saline, aqueous glucose and glycol, while additionally containing a stabilizer and a preservative. The examples of a suitable stabilizer may be an anti-oxidant such as sodium hydrogen sulfite, sodium sulfite, and ascorbic acid. The examples of a suitable preservative may be benzalkonium chloride, methyl- or prophyl-paraben, and chlorobutanol. Other pharmaceutically acceptable carriers may be found in Remington's Pharmaceutical Sciences, 19th ed., Mack Publishing Company, Easton, Pa., 1995.

The pharmaceutical composition for preventing and treating inflammatory skin diseases and autoimmune diseases may be administered to mammals including humans by any route, for example, oral or parenteral routes. The parenteral route includes, but is not limited to, intravenous, intramuscular, intraarterial, intramarrow, intradural, intracardiac, intradermal, subcutaneous, intraperitoneal, intranasal, intragastrointestinal, topical, sublingual or intrarectal. The pharmaceutical composition may be administered through an intradermal route according to some embodiments. As used herein, the term "intradermal" refers to administering the pharmaceutical composition to the cells or the skin of a subject, through the skin of the subject. For instance, the pharmaceutical composition according to the present disclosure may be prepared into an injectable formulation, and then administered by lightly pricking the skin with a 30 gauge thin injection needle. Alternatively, it may be directly applied to the skin of the subject.

The pharmaceutical composition may be prepared into a formulation for oral or parenteral administration, according to the administration routes as described above.

In case of the oral formulation, the composition of the present disclosure may be formulated into powders, granules, tablets, pills, sugar-coated tablets, capsules, liquids, gels, syrups, slurries, and emulsions by using the methods known in the art. For instance, the oral formulation may be prepared into the form of a tablet or a sugar-coated tablet by mixing the active ingredient of the present disclosure with a solid excipient, followed by being ground, mixed with a suitable additive, and processed into a granule mixture. Examples of a suitable excipient include sugars including lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethylcellulose; and fillers including gelatin and polyvinylpyrrolidone. In addition, if desired, cross-linked polyvinylpyrrolidone, agar, alginic acid or sodium alginate may be added as a stabilizer. Further, the pharmaceutical composition according to the present disclosure may further comprise an anti-coaglutinating agent, a lubricant, a wetting agent, a flavoring agent, an emulsifying agent and a preservative.

In case of the parenteral formulation, the composition of the present disclosure may be formulated into injections, creams, lotions, ointments, oils, humectants, gels, aerosols and nasal inhalers by the methods known in the art. These formulations are described in the *Remington's Pharmaceutical Science*, 15th Edition, 1975, Mack Publishing Company, Easton, Pa., which is well known in the pharmaceutical chemistry field.

The total effective amount of the phytosphingosine derivative according to the present disclosure may be administered to a patient in a single dose or in multiple doses with a fractionated treatment protocol. The pharmaceutical composition of the present disclosure may contain variable amount of the active ingredient according to the disease severity. The total effective amount of the phytosphingosine derivative according to the present disclosure is generally about 0.01 μg to 1,000 mg/kg body weight/day, or in some embodiments about 0.1 μg to 100 mg/kg body weight/day. However, the dose of the phytosphingosine derivative may be suitably determined by considering various factors, such as age, body weight, health condition, sex, disease severity, diet, and excretion of a subject in need of treatment, as well as administration frequency and administration route. When those factors are considered, the skilled person in the art may determine the appropriate dose of the phytosphingosine derivative for a certain use as an immune function enhancer. The pharmaceutical composition is not limited in terms of types of formulation, administration routes, and administration methods, as long as it possesses the effectiveness according to the present disclosure.

The composition according to the present disclosure is effective in preventing and treating diseases due to the decrease in immune function. Examples of the diseases due to the decrease in immune function are preferably selected from the group consisting of infectious diseases such as colds, inflammatory diseases, allergic diseases such as atopy, autoimmune disease, hyperkeratotic disorders, chronic fatigue, and cancer, but are not limited thereto. Thus, all the diseases due to the decrease in immune function known to those skilled in the art are included in the present disclosure.

As used herein, the inflammatory skin diseases, autoimmune diseases, and hyperkeratotic disorders include atopic dermatitis, psoriasis, rheumatoid arthritis, systemic sclerosis, systemic lupus erythematosus, asthma, ulcerative colitis, Crohn's disease, multiple sclerosis, contagious dermatitis, allergic skin diseases, acne, urticaria, chronic eczema, lichen planus, actinic keratosis, seborrheic keratosis, ichthyosis, and the like.

The present disclosure provides a method for preparing the phytosphingosine derivative, the method comprising: (a) reacting phytosphingosine (PS) with maleic anhydride (MA) or fumaric acid (FA) in an organic solvent; and (b) separating the phytosphingosine derivative from the resulting reaction product.

Maleic anhydride is the geometric isomer (having the same molecular formula) of fumaric acid, and is important as a raw material for organic synthesis. It is also used as a raw material for plasticizers, polyester resins and fibers, paints, agrochemicals, synthetic detergents, leather, and the like. Representative examples of the organic solvent for the organic synthesis may include methanol, ethanol, butanol, chloroform, dichloromethane, ethyl acetate, hexane, benzene, and the like. The above listed solvents may be used alone or in a mixture thereof.

Herein, for the organic synthesis of phytosphingosine and maleic anhydride or fumaric acid, a 3:1 mixture (v/v, 12.4 ml) of dichloromethane and N,N-dimethylformamide was used at a room temperature. The mixture was stirred at a room temperature for 24 hours to react phytosphingosine with maleic anhydride or fumaric acid. The solvent was then removed through evaporation under reduced pressure, and the residual organic material was dissolved in ether to extract crystallized phytosphingosine derivative.

As used herein, the term "subject" refers to animals, preferably mammals, particularly animals including humans. In addition, the subject may also be a cell, a tissue or an organ derived from an animal. The subject may be a patient in need of treatment. As used herein, the expression "subject in need thereof" refers to a subject who is in need of preventing and treating inflammatory skin diseases, autoimmune diseases and hyperkeratotic diseases.

As used herein, the term "effective amount" refers to the amount of the phytosphingosine derivative that exhibits a desired effect, i.e. the effect of preventing and treating inflammatory skin diseases, autoimmune diseases and hyperkeratotic diseases.

The inventive method for preventing and treating inflammatory skin diseases, autoimmune diseases and hyperkeratotic diseases, includes administering an effective amount of the phytosphingosine derivative to a subject in need thereof, may preferably be a method that uses any type of formulation which is prepared for preventing and treating inflammatory skin diseases, autoimmune diseases and hyperkeratotic diseases, and comprises the phytosphingosine derivative or its pharmaceutically acceptable salt, as an active ingredient.

As set forth above, the present disclosure provides novel phytosphingosine derivatives, and a composition comprising the same for preventing and treating inflammatory skin diseases, autoimmune diseases, and hyperkeratotic diseases. The phytosphingosine derivatives are involved in the expression and generation of transcriptional factors and inflammatory mediators associated inflammation, autoimmune diseases, and hyperkeratotic disorder, along with relevant signaling mechanisms, and the expression and the activation of relevant enzymes, and the like. Thus, the phytosphingosine derivatives are effective in preparing a therapeutic agent and the like possessing excellent comparativeness in the prevention, amelioration, and treatment of inflammatory skin diseases, autoimmune diseases, and hyperkeratotic diseases, in comparison with the conventional phytosphingosine.

Hereinafter, the present disclosure will be described in detail with reference to the following examples. However, the following examples are presented merely for illustrating the present disclosure and are not intended to limit the scope of the present disclosure.

Example 1

Synthesis of the Phytosphingosine Derivatives of Present Disclosure and Analysis of their Structures <1-1> Synthesis of Phytosphingosine Derivatives

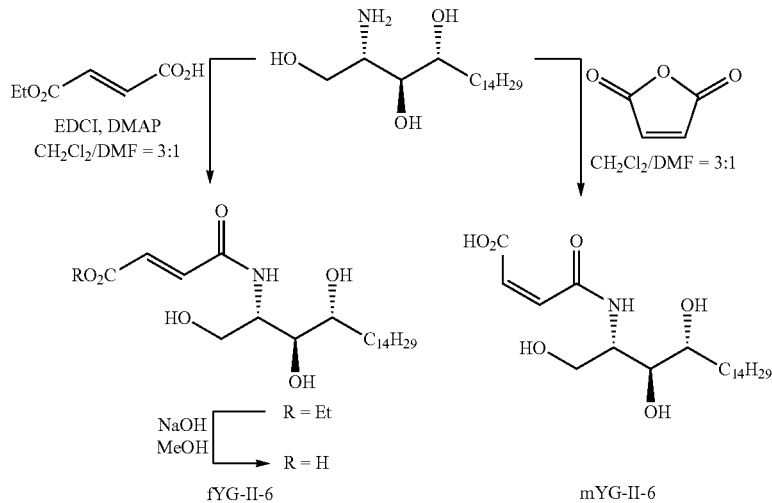

(Z)-4-oxo-4-(((2S,3S,4R)-1,3,4-trihydroxyoctadecan-2-yl)amino)but-2-enoic acid (mYG-II-6) was synthesized by adding maleic anhydride (49 mg, 0.50 mmol, 1.0 equiv) to a solution of phytosphingosine (160 mg, 0.50 mmol, 1.0 equiv) in CH$_2$Cl$_2$/N,N-dimethylformamide (DMF, 3:1, v/v, 5 mL). After being stirred at a room temperature for 24 hours, the reaction mixture was evaporated and the residue was crystallized from diethyl ether. Th white precipitate was filtered, rinsed with diethyl ether, and then dried to give mYG-II-6 (177 mg, 85%) as a white solid.

(E)-4-oxo-4-(((2S,3S,4R)-1,3,4-trihydroxyoctadecan-2-yl)amino)but-2-enoic acid (fYG-II-6) was synthesized by adding ethyl fumaric acid or (E)-4-ethoxy-4-oxobut-2-enoic acid (236 mg, 1.64 mmol, 1.0 equiv), 1-ethyl-3-(3-dimethylaminopropyl)carbodiimide (EDCI, 345 mg, 1.80 mmol, 1.1 equiv), and 4-dimethylaminopyridine (DMAP, 20 mg, 0.16 mmol, 0.1 equiv) to a solution of phytosphingosine (520 mg, 1.64 mmol, 1.0 equiv) in CH$_2$Cl$_2$/N,N-dimethylformamide (DMF, 3:1, v/v, 16 mL). After being stirred at a room temperature for 4 hours, the reaction mixture was evaporated and the resultant crude mixture was purified by flash column chromatography on silica gel (EtOAc/hexane/CH$_2$Cl$_2$, 3:1:1) to give fYG-II-6-ethylester (836 mg, 87%) as a white solid. A solution of NaOH (1.0 M, 1.2 mL, 2.0 equiv) was added to a solution of ethyl ester (270 mg, 0.61 mmol, 1.0 equiv) in MeOH (20 mL). The mixture was stirred at a room temperature for 2 hours, and the reaction was acidified by adding a solution of 1.0 M HCl until reaching a pH of 2. The white precipitate was filtered, rinsed with hexane, and then dried to give fYG-II-6 (228 mg, 90%) as a white solid <1-2> Structures of the Phytosphingosine Derivatives $^1$H NMR analysis data of synthetic compound YG-II-6 are as follows:

$^1$H NMR of mYG-II-6: (DMSO-d$_6$, 400 MHz) d 15.74 (s, 1H), 9.23 (br s, 1H), 6.52 (br s, 1H), 6.24 (d, J=12.7 Hz, 1H), 4.81 (d, J=6.0 Hz, 1H), 4.61 (s, 1H), 4.46 (d, J=6.3 Hz, 1H), 4.13-4.05 (m, 1H), 3.71-3.63 (m, 1H), 3.56-3.49 (m, 1H), 1.56-1.36 (m, 2H), 1.32-1.14 (m, 24H), and 0.87-0.82 (m, 3H).

$^1$H NMR of fYG-II-6: (DMSO-d$_6$, 400 MHz) d 12.75 (br s, 1H), 8.28 (d, J=8.8 Hz, 1H), 7.05 (d, J=15.8 Hz, 1H), 6.50 (d, J=15.4 Hz, 1H), 4.66 (d, J=5.6 Hz, 1H), 4.54 (dd, J=5.08, 5.16 Hz, 1H), 4.05-3.88 (m, 1H), 3.63-3.60 (m, 1H), 3.54-3.48 (m, 1H), 3.41-3.37 (m, 2H), 3.26-3.23 (m, 1H), 1.53-1.41 (m, 3H), 1.23 (s, 24H), and 0.85 (t, J=6.2 Hz, 3H).

Example 2

Comparison of Treatment Efficacy on Inflammatory Skin Diseases and Autoimmune Diseases Between the Phytosphingosine Derivatives and Phytosphingosine <2-1> Inhibitory Effect on the Signaling of Transcriptional Nuclear Factor-κB (NF-κB)

NF-κB serves as a transcriptional factor that plays an important role in the immune response to external stimuli under normal conditions. However, NF-κB increases the expression of specific genes when excessively activated by abnormal stimulation. In particular, NF-κB plays important roles in the development and progression of tumors and autoimmune diseases including chronic inflammation, by increasing the expression of various inflammatory mediators (including prostaglandin and other eicosanoids) causing inflammatory response to activate excessive inflammatory responses. Therefore, regulating the activity of NF-κB activated in association with these diseases is an important target to ameliorate or treat various diseases including inflammatory diseases, autoimmune diseases, and cancers, by regulating initial procedures of several inflammatory responses in the body.

Herein, in order to verify the effect of novel synthetic YG-II-6 compounds and their lead compound, phytosphingosine, on phosphorylation and degradation of IκBα, which is a protein that inhibits the activity of NF-κB by forming a complex with NF-κB, skin keratinocytes were pre-treated with respective compounds for 1 hour and then stimulated with 400 nM TPA for 15 minutes and 30 minutes, respectively. In order to verify the phosphorylation of NF-κB and the expression level of NF-κB in the cytoplasm and nucleus, skin keratinocytes were stimulated for 15 minutes and 1 hour, respectively. The results were confirmed by western blot analysis. In addition, the nuclear translocation of NF-κB was confirmed through reaction with antibodies, fluorescent labeling, and direct observation by microscopy. In order to verify the activity of the respective compounds at the transcription stage, cells were transfected with plasmids labeled with NF-κB luciferase reporter, and the luciferase activity was measured by the luciferase assay. In addition, the phosphorylation of IκBα and NF-κB was measured in the PTA-stimulated mouse skin.

As a result, as can be seen in FIG. 1A, the two YG-II-6 compounds as well as phytosphingosine inhibited the phosphorylation of IκBα and NF-κB, which was increased by TPA stimulation, in skin keratinocytes. In particular, both of the two YG-II-6 compounds exhibited a greater inhibitory effect at a concentration of 10 μM, in comparison with phytosphingosine.

As can be seen from FIG. 1B showing immunostaining results of the nuclear translocation of NF-κB which is freed by IκBβ phosphorylated and degraded by TPA stimulation, both of the two YG-II-6 compounds as well as phytosphingosine inhibited the nuclear translocation of NF-κB, while the two YG-II-6 compounds exhibited a greater inhibitory effect than phytosphingosine.

As can be seen from FIG. 1C, when the activity of the respective compounds at the transcription stage was confirmed by NF-κB luciferase activity, both of the two YG-II-6 compounds as well as phytosphingosine inhibited the luciferase activity increased by TPA stimulation, while the two YG-II-6 compounds exhibited a greater inhibitory effect than phytosphingosine.

In addition, the inhibitory effect of the two YG-II-6 compounds on the phosphorylation of IκBα and NF-κB was confirmed to be greater than that of phytosphingosine in an animal model using mice as well as the cellular level through western blot assay.

Therefore, it is understood that the novel YG-II-6 compounds as well as their lead compound, phytosphingosine, inhibited the phosphorylation and the degradation of IκBα and thus inhibited the activation of NF-κB. However, the inhibitory effect of the novel YG-II-6 compounds on the NF-κB activation was greater than that of phytosphingosine, while fYG-II-6 exhibited a relatively greater inhibitory effect than mYG-II-6.

<2-2> Inhibitory Effect on the Expression of Various Inflammatory Mediators

In order to verify the effect of YG-II-6 compounds and phytosphingosine on the expression of inflammatory mediators regulated by NF-κB activation, skin keratinocytes were treated with the respective compounds for 6 hours, and their effects on the expression of various inflammatory mediators including cytokines were measured by real-time PCR.

As can be seen from the results of FIG. 2, the two YG-II-6 compounds exhibited an excellent inhibitory effect on the expression of IL-1α, L-6, IL-8, and TNF-α, which are representative inflammatory mediators of which expression is increased by NF-κB activation, along with an excellent inhibitory effect on mRNA expression of COX-2 enzyme. Further, the inhibitory effects of the two YG-II-6 compounds on these inflammatory mediators were relatively greater than those of the lead compound, phytosphingosine. Therefore, it was verified that novel synthetic compounds, two YG-II-6 compounds, can suppress inflammatory responses by inhibiting the NF-κB activation, and thus, inhibit the expression of inflammatory mediators, while possessing a greater inhibitory effect than the control compound, phytosphingosine.

<2-3> Inhibitory Effect on JAK/STAT Signaling

The JAK/STAT signaling pathway is activated by stimulations such as various cytokines and growth factors, playing various roles such as differentiation, growth, and survival of cells. However, when being activated by factors such as inflammatory mediators generated under abnormal conditions, the JAK/STAT signaling pathway may cause various diseases such as autoimmune diseases including rheumatoid arthritis and cancer diseases. Therefore, the inhibition or regulation of the JAK/STAT signaling pathway activated under abnormal conditions as well as NF-κB abnormally activated in association with the above mentioned diseases plays an important role in the prevention and treatment of inflammation and autoimmune diseases.

In order to verify the effects of novel synthetic YG-II-6 compounds and their lead compound, phytosphingosine, on the JAK/STAT signaling, various cells were used. These cells were treated with respective compounds at corresponding concentrations for 1 hour. Then, stimulation was performed on the skin keratinocytes using 400 nM of TPA for 3 hours or 100 U/ml of IFN-γ for 15 minutes (FIG. 3A); human peripheral blood mononuclear cells using 10 ng/ml of IL-6 for 15 minutes (FIG. 3B); mouse T cells using 100 U/ml of IFN-γ for 15 minutes (FIG. 3C), using 10 ng/ml of IL-6 for 10 minutes (FIG. 3D), and using 50 ng/ml of IL-2 for 15 minutes (FIG. 3E); and mouse-derived lymphoma cells using 100 ng/ml of prolactin (PRL) or IL-2 for 10 minutes (FIGS. 3F and 3G). In addition, in order to verify the activation of JAK and STAT, proteins were separated and subjected to electrophoresis. The phosphorylation of the respective proteins was confirmed by western blot assay.

As for the verification on the effects of the respective compounds on the JAK/STAT signaling in the human-derived skin keratinocytes, the YG-II-6 compounds effectively inhibited the phosphorylation of JAK1, JAK2, STAT1, and STAT3 proteins of which the phosphorylation was increased by TPA or IFN-γ stimulation (See FIG. 3A). In addition, the results showing the effects of the respective compounds on the phosphorylation of STAT1 and STAT3 in IL-6-stimulated human peripheral blood mononuclear cells verified that both of the YG-II-6 compounds effectively inhibited the phosphorylation thereof (See FIG. 3B).

In addition, when the JAK/STAT signaling pathway was activated by the stimulation of various cytokines in the mouse-derived T cells, both of the YG-II-6 compounds effectively inhibited the phosphorylation of STAT proteins activated by the respective stimulations (See FIG. 3C to FIG. 3E).

In addition to when the JAK/STAT signaling pathway was activated by the application of various stimulations to normal cells, when rat-derived lymphoma cells known to be associated with lymphoma, were stimulated with prolactin or IL-2, to activate the JAK2/STAT5 or JAK3/STAT5 pathway, both the YG-II-6 compounds effectively inhibited the phosphorylation of STAT5 proteins activated by the two pathways (See FIGS. 3F and 3G).

Taken together the above results on the JAK/STAT signaling, the two YG-II-6 compounds as novel compounds effectively inhibited the JAK/STAT signaling pathway activated by various stimulations, and the inhibitory effects thereof were relatively greater than that of the lead compound, phytosphingosine.

<2-4> Inhibitory Effect on MAP Kinase

The MAP kinase signaling pathway plays a key role in the differentiation, growth, and survival of cells, while its activation has been confirmed in various diseases including inflammatory diseases.

In order to verify the effects of the respective compounds on MAP kinase, skin keratinocytes were treated with the respective compounds for 1 hour, and then stimulated with 400 nM TPA for 15 minutes. The level of phosphorylation was confirmed by western blot assay.

As can be seen from FIG. 4, both of the two YG-II-6 compounds effectively inhibited the phosphorylation of ERK1/2, p38, and JNK. However, phytosphingosine exhibited a relatively weaker inhibitory activity than the YG-II-6 compounds.

<2-5> Effect on TPA-Induced Skin Inflammatory Diseases

For the animal model of inflammatory response caused by skin irritation, the mouse skin was stimulated with TPA. First, the hairs on the dorsal skin of C57BL/6 mice were removed, and on the next day, 1000 µL of each of the compound samples was applied on the hairless dorsal area. After 1 hour, the dorsal area applied with the compound sample was irritated with 100 µL of 8.1 µM TPA dissolved in acetone. After 24 hours, the application of the compound sample and TPA was repeated once more using the same method. After 1 hour, the skin of the tested mouse was collected. The thickness and swelling degree of the collected skin were measured, and its histopathological change was observed through hematoxylin and eosin (H&E) staining. In addition, the dorsal area of the hairless mice was treated with the fYG-II-6 compound, followed by the application of TPA, and then a tape was attached on the dorsal skin. After 24 hours, the level of inflammatory response on the dorsal skin of the tested mouse was confirmed by PCNA and hematoxylin & eosin (H&E) staining.

TPA stimulation caused typical inflammatory response on the skin of C57BL/6 mice. That is, it was confirmed that the proliferation of skin keratinocytes remarkably increased epidermal hyperplasia (=acanthosis) which leads to the thickening of the skin, hyperkeratosis, and translocation of inflammatory cells into the dermal area.

However, as can be seen from the results of FIGS. 5A to 5C, the treatment with respective compound samples effectively inhibited the histopathological changes associated with the inflammatory response and the translocation of inflammatory cells into the dermal area. In particular, the inhibitory activities of the YG-II-6 compounds were much greater than that of phytosphingosine. As can be seen from H&E staining results, the treatment with the compounds remarkably reduced the increase in skin thickness caused by the inflammatory response, due to the stimulation, in addition to the histopathological change. This inhibitory activity was much greater in the YG-II-6 compounds than the lead compound, phytosphingosine. Also, a patch test using hairless mice showed that this efficacy was similar to that of TPA-stimulated C57BL/6 mice (FIG. 5D).

Taken together the above results, the inhibitory activity of the YG-II-6 compounds on the skin inflammatory response was greater than that of phytosphingosine, also in the TPA-stimulated skin inflammatory disease animal model.

<2-6> Effect of YG-II-6 on IL-23-Induced Psoriasiform Dermatitis

The injection of IL-23 into the mouse ear induces diseases similar to psoriasis as one of the autoimmune diseases. Thus, in order to verify the effects of the test compounds on psoriasis, psoriasiform dermatitis was induced by using IL-23. In other words, 10 µL of IL-23 (500 ng) was intradermally injected into the ears of C57BL/6 mice every other day for a total of seven times over 12 days. The ear thickness was measured 24 hours after the final injection. The mouse ears were collected and then subjected to histological photography. RNA was isolated from the ears of the mice, and the expression of genes associated with psoriasis was confirmed by real-time PCR.

As can be seen from FIGS. 6A and 6B, the thickness of the mice ears was remarkably increased by IL-23 stimulation as compared with the normal group administered with PBS.

As seen from histological results by H&E staining, epidermal hyperplasia (=acanthosis), hyperkeratosis, and the translocation of inflammatory cells into the dermal area, which are known as lesions of psoriasis disease, were remarkably increased. However, the YG-II-6 compounds effectively inhibited histopathological changes in these psoriasis disease lesions as confirmed in FIG. 6B.

In addition, the IL-23 stimulation remarkably increased the expression of various disease-mediated inflammatory factors such as various cytokines and chemokines associated with psoriasis diseases, whereas the YG-II-6 compounds remarkably inhibited the expression of these genes. This effect can be confirmed from FIG. 6C showing the results of inhibiting the expression of various inflammatory factors.

Similar to the IL-23-induced psoriasis diseases animal models, in the psoriasiform dermatitis cell model obtained by stimulating human-derived keratinocytes with IL-22, the YG-II-6 compounds inhibited the expressions of five chemokines (CXCL1, CXCL10, CCL17, CCL20, and CCL27), which are representative factors associated with psoriasis diseases (See FIG. 6D).

Therefore, the YG-II-6 compounds were shown to have inhibitory activities on diseases by inhibiting the expressions of various factors associated with inflammation in the autoimmune disease model as well as TPA-induced skin inflammatory model.

<2-7> Verification on Effect on Apoptosis

It has been known that phytosphingosine generally possesses an excellent inhibitory efficacy in association with skin diseases, but has a limitation to its clinical application due to its significantly strong toxicity. Therefore, in order to verify the degree of the cytotoxicity of the YG-II-6 compounds, their cytotoxicity on human-derived keratinocytes was confirmed by using the WST-1 reagent. In order to verify the effects of the compounds on the expression of proteins associated with apoptosis, the keratinocytes were treated with corresponding concentrations of the respective compound samples and stimulated with TPA for 24 hours, and the expression levels of proteins were confirmed by western blot assay. In addition, human-derived keratinocytes and primary culture skin keratinocytes were treated with the compounds, and after 24 hours, subjected to FITC staining and TUNEL assay, and the skin tissues isolated from TPA-induced mice was subjected to FITC staining Phytosphingosine showed its strong cytotoxicity at 5-10 μM, whereas the two YG-II-6 compounds exhibited cytotoxicity at around 20 μM. Thus, the two YG-II-6 compounds are considered less cytotoxic than the lead compound, phytosphingosine (See FIG. 7A). As for the signaling associated with apoptosis, it can be confirmed that the YG-II-6 compounds increased the fragmentation of PARP and caspase-3, which are known as representative markers of apoptosis; inhibited the expression of p21 and p27, which are cell cycle regulatory factors; increased the expression of Bax and Bad; and inhibited the expression of cyclin D1 and E (See FIG. 7B). In order to verify the effects of samples on apoptosis, cells treated with the compound samples were subjected to FITC staining and TUNEL assay and the collected skin tissues were subjected to FITC staining. As can be seen from the results of FIGS. 7C to 7E, the YG-II-6 compounds as well as phytosphingosine induced apoptosis in the TPA-stimulated cells and the mouse skin tissues, while the effect of the YG-II-6 compounds was greater than phytosphingosine.

What is claimed is:

1. A phytosphingosine derivative as represented by the following Chemical Formulas IA or IB:

[Chemical Formula IA]

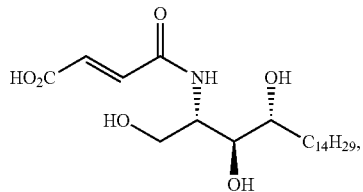

[Chemical Formula IB]

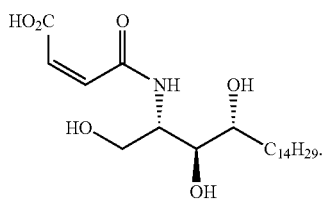

2. A pharmaceutical composition, comprising the phytosphingosine derivative of claim 1 or a pharmaceutically acceptable salt thereof, as an active ingredient.

3. The composition of claim 2, wherein the phytosphingosine derivative is used for treating psoriasis.

4. A method for preparing the phytosphingosine derivative of claim 1, the method comprising:

reacting phytosphingosine with maleic anhydride or fumaric acid, in an organic solvent; and separating the phytosphingosine derivative of claim 1 from the resulting reaction product.

5. The method of claim 4, wherein the organic solvent comprises a 3:1 mixture (v/v) of dichloromethane and N,N-dimethylformamide.

6. A method for preventing and treating psoriasis, comprising administering to a subject in need thereof an effective amount of the phytosphingosine derivative of claim 1, or a pharmaceutically acceptable salt thereof.

* * * * *